United States Patent
Chen et al.

(10) Patent No.: US 10,226,255 B2
(45) Date of Patent: Mar. 12, 2019

(54) MEDICAL ANASTOMOSIS DEVICE

(71) Applicant: Touchstone International Medical Science Co., Ltd., Jiangsu (CN)

(72) Inventors: Wangdong Chen, Jiangsu (CN); Shuicheng Ding, Jiangsu (CN); Yanbo Shi, Jiangsu (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 335 days.

(21) Appl. No.: 15/278,961

(22) Filed: Sep. 28, 2016

(65) Prior Publication Data

US 2017/0014134 A1 Jan. 19, 2017

Related U.S. Application Data

(63) Continuation of application No. PCT/CN2015/075828, filed on Apr. 3, 2015.

(30) Foreign Application Priority Data

Apr. 4, 2014 (CN) .......................... 2014 1 0135296
Mar. 13, 2015 (CN) .......................... 2015 1 0112664

(51) Int. Cl.
| | |
|---|---|
| A61B 17/072 | (2006.01) |
| A61B 17/115 | (2006.01) |
| A61B 17/068 | (2006.01) |
| A61B 90/00 | (2016.01) |
| A61B 17/29 | (2006.01) |

(52) U.S. Cl.
CPC ........ *A61B 17/1155* (2013.01); *A61B 17/068* (2013.01); *A61B 17/072* (2013.01);
(Continued)

(58) Field of Classification Search
CPC ............... A61B 17/068; A61B 17/072; A61B 17/07207; A61B 17/115; A61B 17/1155;
(Continued)

(56) References Cited

U.S. PATENT DOCUMENTS 4,665,916 A * 5/1987 Green ................. A61B 17/072 227/178.1
5,100,042 A * 3/1992 Gravener ............ A61B 17/072 227/176.1
(Continued)

FOREIGN PATENT DOCUMENTS

| CN | 101856251 A | 10/2010 |
|---|---|---|
| CN | 201719300 U | 1/2011 |

(Continued)

OTHER PUBLICATIONS

International Search Report, dated Jul. 13, 2015, for International Application No. PCT/CN2015/075828, 3 pages.

*Primary Examiner* — Scott A. Smith
(74) *Attorney, Agent, or Firm* — Seed IP Law Group LLP

(57) ABSTRACT

A medical anastomosis device (100), having a firing assembly (50), a staple anvil (30), a staple anvil assembly (34), and a staple cartridge assembly (32); the firing assembly (50) includes a staple cartridge push rod (54) provided with a stop pin (542) thereon; the staple anvil (30) is provided with a safety block (38) therein capable of coordinating with the stop pin (542); the safety block (38) is provided with a clamping groove (384) thereon; when the anastomosis device (100) is in an initial status, the safety block (38) and the stop pin (542) do not contact each other; when the anastomosis device (100) is in a firing status, the movement of the safety block (38) is restricted, and the clamping groove (384) is located on a movement route from the distal end of the medical anastomosis device (100) to the proximal end; and when the anastomosis device (100) returns to the initial status after being fired, the stop pin (542) is clamped in the clamping groove (384), and the safety block (38) limits the stop pin (542) in the direction from the proximal end of the medical anastomosis device (100) to the distal end. The three status jointly compose the complete firing (Continued)

process of the staple cartridge assembly (32), preventing a second firing of the staple cartridge push rod (54) to ensure operation safety.

17 Claims, 16 Drawing Sheets

(52) U.S. Cl.
CPC ............... *A61B 17/07207* (2013.01); *A61B 2017/07214* (2013.01); *A61B 2017/07221* (2013.01); *A61B 2017/07271* (2013.01); *A61B 2017/2946* (2013.01); *A61B 2090/0801* (2016.02); *A61B 2090/0814* (2016.02)

(58) Field of Classification Search
CPC ........... A61B 2017/07214; A61B 2017/07271; A61B 2017/2946; A61B 2090/0801; A61B 2090/0814
USPC .. 227/19, 175.1, 175.2, 175.3, 176.1, 180.1; 606/139, 153, 219
See application file for complete search history.

(56) References Cited

U.S. PATENT DOCUMENTS

| | | | |
|---|---|---|---|
| 5,116,349 A | 5/1992 | Aranyi | |
| 5,413,267 A * | 5/1995 | Solyntjes | A61B 17/072 227/175.4 |
| 5,462,215 A * | 10/1995 | Viola | A61B 17/072 227/176.1 |
| 5,470,006 A | 11/1995 | Rodak | |
| 5,470,009 A * | 11/1995 | Rodak | A61B 17/072 227/176.1 |
| 5,735,445 A * | 4/1998 | Vidal | A61B 17/072 227/175.4 |
| 6,988,650 B2 * | 1/2006 | Schwemberger | A61B 17/072 227/176.1 |
| 7,147,139 B2 * | 12/2006 | Schwemberger | A61B 17/072 227/181.1 |
| 7,641,092 B2 * | 1/2010 | Kruszynski | A61B 17/072 227/175.2 |
| 8,353,436 B2 * | 1/2013 | Kasvikis | A61B 17/072 227/175.1 |
| 2005/0173490 A1* | 8/2005 | Shelton, IV | A61B 17/07207 227/175.2 |
| 2007/0278277 A1* | 12/2007 | Wixey | A61B 17/0686 227/175.2 |

FOREIGN PATENT DOCUMENTS

| | | |
|---|---|---|
| CN | 102599954 A | 7/2012 |
| CN | 202619744 U | 12/2012 |
| CN | 103860230 A | 6/2014 |
| CN | 203776964 U | 8/2014 |
| JP | 2002-165801 A | 6/2002 |

* cited by examiner

MEDICAL ANASTOMOSIS DEVICE

TECHNICAL FIELD

The present disclosure relates to a technical field of medical apparatus manufacturing, more particularly to a medical anastomosis device.

BACKGROUND

Usually, when an anastomosis device has completed cutting and anastomosing actions, the doctor needs to press a release button to open the stapler, which makes the staple cartridge and the cutter return back to the initial position so as to facilitate taking out the stapler from the operative site.

However, due to some careless or inexperienced doctors, it may cause mistaken fire by triggering the firing handle again after a completed fire, or it may cause wrongly using a stapler which has been fired in a following cutting and anastomosing operation, which can cause medical negligence.

SUMMARY

An embodiment provides an anastomosis device which facilitates preventing secondary firing once it has been fired.

In an embodiment a medical anastomosis device includes a firing assembly, an anvil seat, an anvil assembly and a staple cartridge assembly. The firing assembly includes a staple cartridge push rod which is provided with a banking pin. The anvil seat includes a safety block to mate with the banking pin, the safety block defining a slot. The firing assembly is used for driving the staple cartridge assembly to move from a proximal end of the anvil seat to a distal end of the anvil seat. When the medical anastomosis device is in an initial status, the safety block does not interfere with or block the banking pin. When the medical anastomosis device is in a firing status, movement of the safety block is restricted, and the slot is located in a movement route of the banking pin when the banking pin moves from a distal end of the medical anastomosis device to a proximal end of the medical anastomosis device. When the medical anastomosis device returns to the initial status after being completely fired, the banking pin is locked in the slot so that the banking pin can be restricted by the safety block along a direction from the proximal end of the medical anastomosis device to the distal end of the medical anastomosis device.

In an embodiment, the anvil seat includes therein a restriction portion to mate with the banking pin. When the medical anastomosis device is in the initial status, the safety block does not interfere with the restriction portion. When the medical anastomosis device is in the firing status, the safety block abuts against the restriction portion.

In an embodiment, the safety block is configured to consistently receive a pivotal force which drives a distal end of the safety block to move toward the proximal end of the medical anastomosis device.

In an embodiment, the anvil seat includes therein a safety block seat to mount the safety block. The safety block is pivotally connected to the safety block seat, and the restriction portion is formed on the safety block seat.

In an embodiment, a flexible member is connected between the safety block and the safety block seat.

In an embodiment, the slot includes therein a guiding face which is so arranged, when the banking pin is locked in the slot, that the banking pin and the slot can be disengaged with each other by the safety block through a force along a mounting direction of the staple cartridge assembly.

In an embodiment, when the staple cartridge assembly is in a firing status, the banking pin is resisted between a distal end of the safety and the slot.

In an embodiment, the safety block is pivotally connected to the anvil seat, and a flexible member is connected between the safety block and the anvil seat.

In an embodiment, the flexible member consistently provides the safety block a pivotal force to drive the distal end of the safety block to move towards the proximal end of the anastomosis device.

In an embodiment, the anvil seat includes therein a detachable safety block seat. The safety block seat is relatively fixed to the anvil seat. The safety block seat is pivotally connected to the anvil seat. The safety block seat is provided with a mounting portion. Two ends of the flexible member are respectively connected to the safety block and the mounting portion.

In an embodiment, the safety block seat includes a first mounting plate and a second mounting plate opposite to the first mounting plate. At least part of the safety block is mounted between the first mounting plate and the second mounting plate.

In an embodiment, the safety block defines a first mounting hole. The first mounting plate and the second mounting plate respectively define a second mounting hole. The medical anastomosis device further includes a pivotal axis which extends through the first mounting hole and the second mounting hole so as to fix relative position of the first mounting hole and the second mounting hole along an axis direction.

In an embodiment, the staple cartridge assembly includes a staple pusher which is provided with a first limiting portion located at a distal end of the banking pin. A distal end of the safety block includes a second limiting portion. When the medical anastomosis device is in the initial status, the second limiting portion of the safety block is interfered with the first limiting portion of the staple pusher.

In an embodiment, the staple pusher defines a cutter slot, and the first limiting portion includes a first part and a second part respectively located at opposite sides of the cutter slot.

In an embodiment, the safety block includes a block body and a locking portion extending from the block body. The locking portion and the block body jointly define the slot. An opening of slot faces towards the proximal end of the medical anastomosis device.

In an embodiment, a side of the locking portion facing a distal end of the block body includes a guiding ridge. An angle between the guiding ridge and the block body is an obtuse angle.

In an embodiment, a connecting portion of the guiding ridge and the block body circular is of arc transition.

Compared to the prior arts, the medical anastomosis device of an embodiment of the present application provides different mating status of the safety block and the banking pin of the staple cartridge push rod to avoid secondary firing. In use, the staple cartridge assembly is firstly mounted to the anvil seat, the safety block is not in contact with the banking pin. The firing assembly can apply force to the staple cartridge assembly and fires the device. When the medical anastomosis device is in a firing status, movement of the safety block is restricted. The slot is located in a movement route of the banking pin when the banking pin moves from a distal end of the medical anastomosis device to a proximal end of the medical anastomosis device, so that the banking pin is locked in the slot when the staple cartridge assembly is pulled back afterwards. When once a cutting and anastomosis is completed, the staple cartridge assembly is pulled back to the proximal end of the anvil seat again, and then the anastomosis device reaches the status of being completely fired. In the process of returning back to this status, the slot of the safety block is gradually locked with the banking pin. As a result, the staple cartridge push rod can be prevented from being fired again so as to ensure the operation safety.

ILLUSTRATED EMBODIMENTS

Detailed description of the present application will be depicted in combination with embodiments shown in figures. It should be noted that the present application should not be restricted to the embodiments, and modifications of structure, method and function to those of ordinary skill in the art according to the embodiments are all included within the protection scope of the present application.

The words used to express locations or directions in describing the embodiments disclosed herein all adopt the appliance operator as reference. An end near the operator is a proximal end and an end away from the operator is a distal end. Meanwhile, in the present application, a bottom side of the anastomosis device is defined as a direction of the handle extending from the housing, and a direction opposite to the bottom side is defined as a top side of the anastomosis device.

Figure 1:
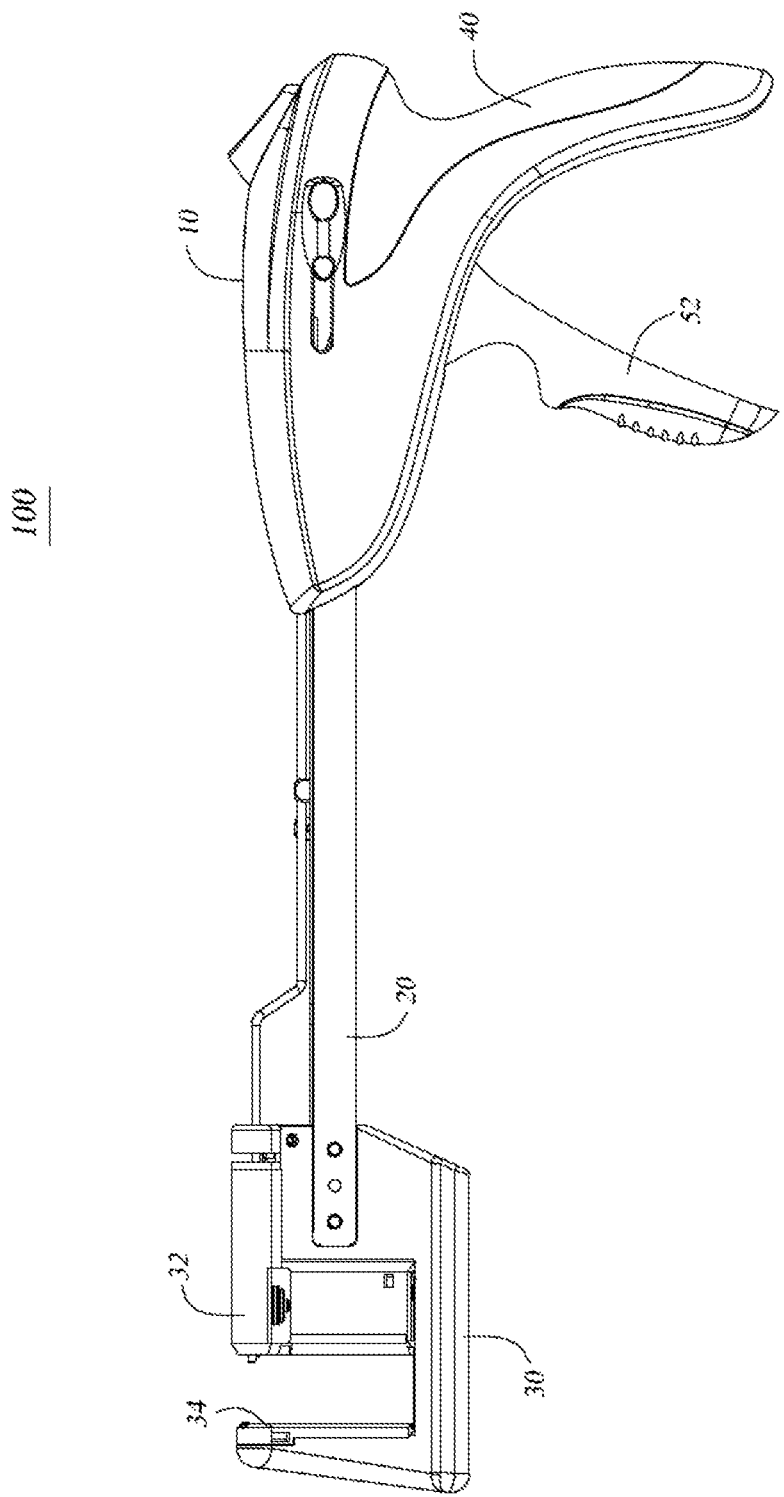
FIG. 1 is a perspective view of a medical anastomosis device in accordance with an illustrated embodiment of the present application.

Referring to FIG. 1, in accordance with an embodiment of the present application, an anastomosis device 100 includes a housing 10, a supporting structure 20 extending to the distal end from the housing 10 and an anvil seat 30 connected to the distal end of the supporting structure 20. The anvil seat 30 is firmly connected to the supporting structure 20. A bottom side of the housing 10 includes a handle 40 located at the proximal end thereof.

The anastomosis device 100 includes a staple cartridge assembly 32 and an anvil assembly 34. In the present embodiment, the staple cartridge assembly 32 and the anvil assembly 34 are detachably assembled to the anvil seat 30, and their shapes are matchable with the shape of the anvil seat 30. For example, cross sections of the staple cartridge assembly 32 and the anvil assembly 34 are of curved shapes which are helpful to anastomosis tissues in a narrower operating space.

Figure 2:
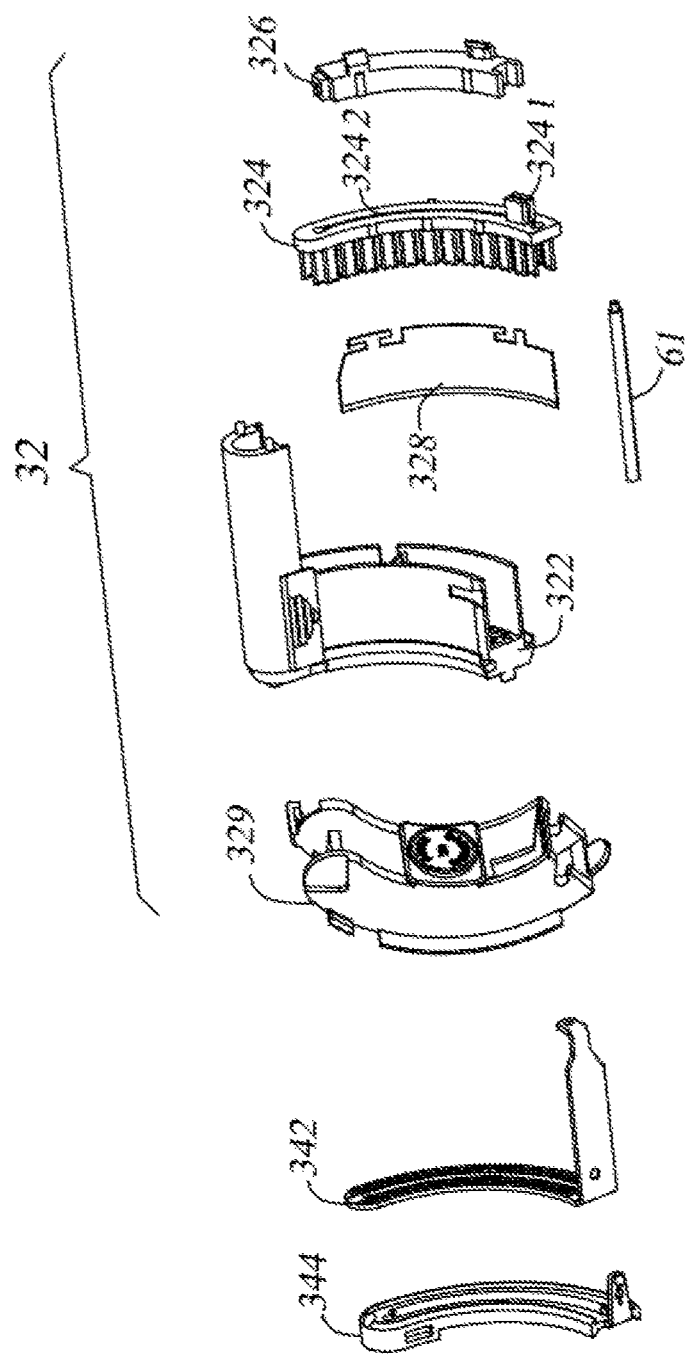
FIG. 2 is an exploded view of the medical anastomosis device with a staple cartridge assembly separated from an anvil assembly.

Referring to FIG. 2, the staple cartridge assembly 32 includes a staple cartridge 322 which includes a staple cartridge surface (not shown) and one or multiple rows of staple receiving slots (not shown) alternately disposed on the surface. The staple cartridge assembly 32 also includes a staple pusher 324 and a cutter assembly disposed in the staple cartridge 322. Staples can be pushed out by the staple pusher 324 from the staple receiving slots. The cutter assembly includes a cutter rest 326 and a cutter 328 disposed on the distal end of the cutter rest 326. The staple cartridge assembly 32 includes a staple cartridge shell 329 for blocking the staples and the cutter 328 which are received in the staple cartridge 322 in order to prevent missing staples and mistakenly firing.

The staple cartridge surface and the staple pusher 324 respectively include a cutter slot 3242 to support firing operation of the cutter 328. In the present embodiment, the staple receiving slots are positioned at both sides of the cutter slot 3242. As a result, in the process of cutting and stapling tissues, broken ends of the dissected tissues can be stapled simultaneously.

Figure 3:
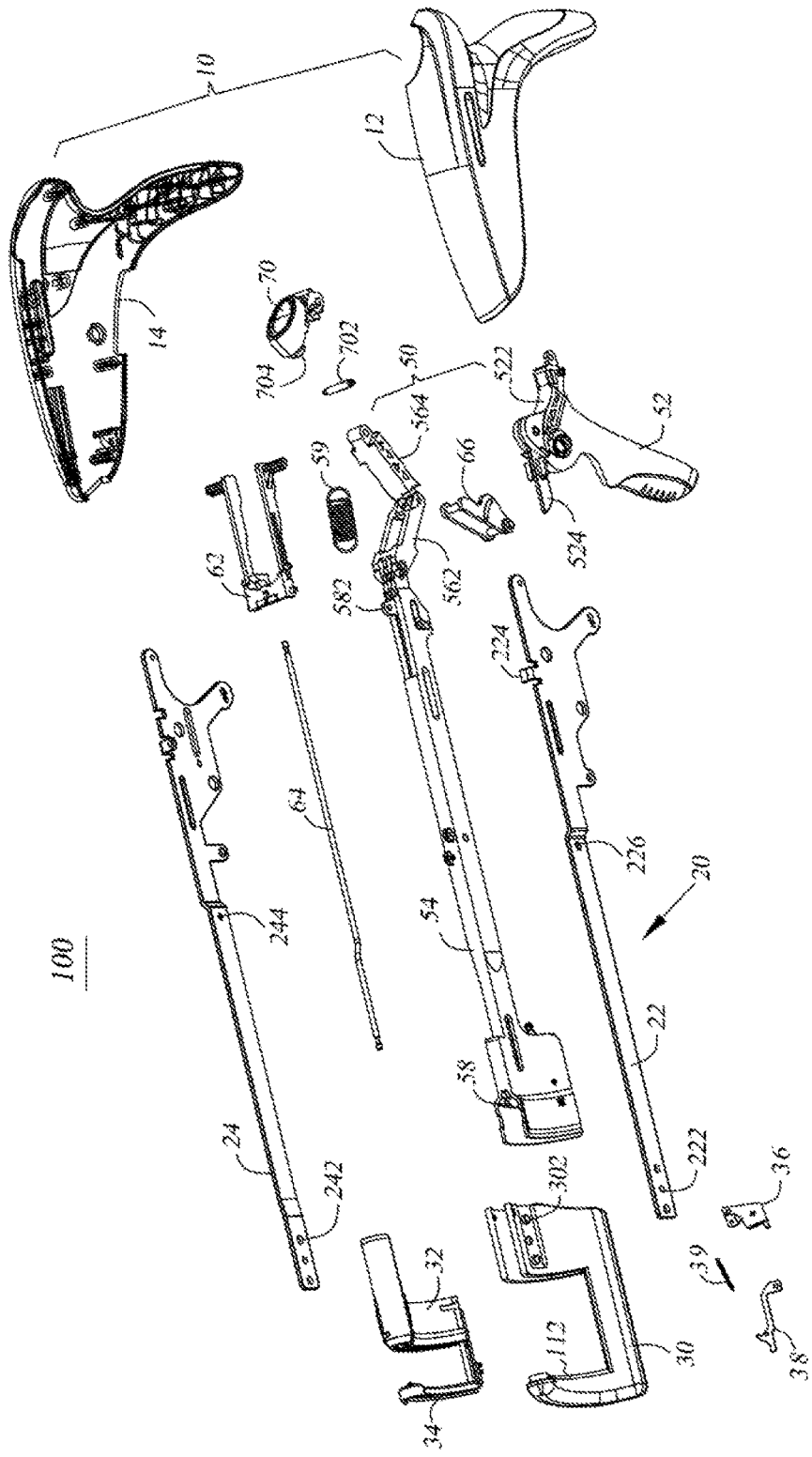
FIG. 3 is an exploded view of the medical anastomosis device in accordance with an illustrated embodiment of the present application.

Referring to FIGS. 2 and 3, in accordance with an embodiment of the present application, the distal end of the staple cartridge assembly 32 is also associated with the anvil assembly 34 which includes an anvil 342 and a cutting pad 344. When the staple cartridge assembly 32 is installed onto the anvil seat 30, the anvil 342 and the cutting pad 344 can be accordingly installed onto the anvil seat 30.

The supporting structure 20 includes a pair of brackets 22, 24. The brackets include a left bracket 22 and a right bracket 24 which are disposed oppositely. Distal ends of the left and right brackets 22, 24 are respectively arranged with mounting holes 222, 242 for mating with a pin hole of the anvil seat 30 and protrusion 302 thereof, so as to fasten the anvil seat 30 and the supporting structure 20 with each other.

The proximal end of the supporting structure 20 is connected to the housing 10. Correspondingly, the housing 10 includes a left half shell 12 and a right half shell 14 for connecting the left and right brackets 22, 24, respectively.

The anastomosis device 100 also includes a firing assembly 50 which includes a firing handle 52 located at the proximal end of the anastomosis device 100, a staple cartridge push rod 54 driven by the firing handle 52 and a transmission member connected with the firing handle 52 and the staple cartridge push rod 54. The staple cartridge push rod 54 can be driven by the firing handle 52 to push the staple cartridge assembly 32 moving from the proximal end of the anastomosis device 100 to the distal end thereof. The staple cartridge assembly 32 is driven toward the anvil assembly 34 and finally the anastomosis device 100 is closed. Under this condition, if physiological tissue is placed between the staple cartridge assembly 32 and the anvil assembly 34, then the staple cartridge assembly 32 can be driven by the staple cartridge push rod 54 toward the anvil assembly 34 for clamping the physiological tissue.

In an embodiment of the present application, the transmission member includes a front link 562 and a rear link 564. The distal end of the front link 562 is pivotally connected to the staple cartridge push rod 54 through a front rod pin (not shown), and the proximal end of the front link 562 is pivotally connected to the distal end of the staple cartridge push rod 54 through a rear rod pin (not shown). The proximal end of the rear link 564 is connected to the supporting structure 20.

Further referring to FIG. 3, the anastomosis device 100 includes an anti-overflow pin assembly which includes an anti-overflow pin push rod 62, a transmission push rod 64 connected to the anti-overflow pin push rod 62 and an anti-overflow pin 61 extending through the staple cartridge assembly 32 (shown in FIG. 2). The anti-overflow pin 61 is connected to the transmission push rod 64 in a linkage manner.

In an embodiment of the present application, the anti-overflow pin push rod 62 is set to a saddle type and provided with symmetrical operating portions at the proximal end thereof. The symmetrical operating portions extend beyond the housing 10.

The anti-overflow pin assembly also includes a rotating crank 66 connected to the anti-overflow pin push rod 62. The rotating crank 66 is pivotally connected to the supporting structure 20 and is also movably connected to the staple cartridge push rod 54. The anti-overflow pin push rod 62 can be pushed from the proximal end to the distal end of the anastomosis device 100 by the operating portion of the anti-overflow pin push rod 62. Meanwhile, when driving the anti-overflow pin push rod 62, the transmission push rod 64 will also be pushed toward the distal end, thus the anti-overflow pin 61 is associated moved to the distal end of the anastomosis device.

An operating process for clamping physiological tissue using the anastomosis device 100 in an embodiment of the present application is as follows:

Under the initial status of the anastomosis device 100, the front link 562 and the rear link 564 are arranged with each other in an angle less than 180 degrees, and the connecting portion of the front link 562 and the rear link 564 abuts against a supporting portion 522 of the firing handle 52.

When it needs to clamp the physiological tissue, firstly, the physiological tissue is positioned between an anvil surface of the anvil assembly 34 and a staple cartridge surface of the staple cartridge assembly 32, and then the anti-overflow pin push rod 62 is pushed to move toward the distal end of the anastomosis device 100. Accordingly, the transmission push rod 64 and the anti-overflow pin 61 will be pushed to move toward the distal end as well. The anti-overflow pin 61 will be driven to extend out from the staple cartridge assembly 32 and ultimately mates with a receiving portion (not shown) of the anvil assembly 34. The opening between the anvil assembly 34 and the staple cartridge assembly 32 is closed, namely the opening of the anvil seat 30 is closed.

Then, the firing handle 52 is driven to pivotally rotate toward the handle 40. Meanwhile, the supporting portion 522 will abut against the connecting portion of the front link 562 and the rear link 564, which forces the front link 562 and the rear link 564 being pivoted relative to each other toward a direction of increasing angle between the two.

In an embodiment of the present application, the front link 562 and the rear link 564 can be driven by the supporting portion 522 to a relative stable status with an angle slightly larger than 180 degrees, and ultimately abut against an abutting portion 224 of the supporting structure 20. Meanwhile, the front link 562 and the rear link 564 move to an interference status.

In such process, a distance limited between the distal end of the front link 562 and the proximal end of the rear link 564 gradually increase to a maximum value and then slightly reduce. The proximal end of the rear link 564 is fixed to the supporting structure 20, the distal end of the front link 562 drives the staple cartridge push rod 54 to move toward the distal end of the anastomosis device 100, the driving force applied to the staple cartridge assembly 32 by the staple cartridge push rod 54 drives the staple cartridge assembly 32 to move toward the anvil assembly 34 so as to clamp the physiological tissue.

In an embodiment of the present application, the firing assembly 50 further includes a pin push rod 58 which is slidably disposed in the staple cartridge push rod 54. Acting surfaces of the pin push rod 58 and the cutter rest 326 are made of shapes fitted each other.

In the present embodiment, the acting surfaces of the pin push rod 58 and the cutter rest 326 are of curved shapes.

The firing handle 52 is connected with a wedged plate 524 which can be at least partially mounted inside the staple cartridge push rod 54 for realizing interaction with the pin push rod 58.

An operating process for cutting and anastomosing physiological tissue using the anastomosis device 100 in an embodiment of the present application is as follows:

After completing the operation of clamping the above-mentioned physiological tissue, the firing handle 52 is driven by a return spring (not shown) to rotate to a direction away from the handle 40 so as to realize automatical reset of the firing handle 52.

In this process, the wedged plate 524 of the firing handle 52 is triggered to abut against the pin push rod 58. Meanwhile, through pivotally rotating the firing handle 52 to a direction toward the handle 40, the pin push rod 58 is pushed by the wedged plate 524 to move to the distal end of the anastomosis device so that the cutter 328 and the staple pusher 324 can be triggered simultaneously. Staples in the staple receiving slots will be driven by the staple pusher 324 to tightly anastomosis the physiological tissue, and corresponding physiological tissue will be cut off by the cutter 328 simultaneously.

The proximal end of the pin push rod 58 includes a holding portion 582 extending beyond the staple cartridge push rod 54. The firing assembly 50 includes an elastic element 59 connected between the holding portion 582 and the supporting structure 20. In an embodiment of the present application, the elastic element 59 is an extension spring.

When the pin push rod 58 moves to the distal end, e.g., the staple cartridge assembly 32 is forced to move toward the anvil assembly 34, e.g., in firing process, the elastic element 59 is in being extended status. After the physiological tissue has been cut and stapled, the pin push rod 58 will be retracted by self-pulling force of the elastic element 59. Meanwhile, the cutter rest 326 provided with the cutter 328 can be accordingly retracted. As a result, the anastomosis device completes the entire firing process and comes to a completely fired status.

After the anastomosis device comes to a completely fired status, the staple cartridge push rod 54 can be driven from the distal end to return back to the initial position by pressing a release button 70. Meanwhile, the anastomosis device will be opened by opening the staple cartridge assembly 32 and the anvil assembly 34 so that the cut and stapled tissue can be easily taken out.

In an embodiment of the present application, the release button 70 is movably connected to the supporting structure 20 by a button release pin 702. Besides, the proximal end of the rear link 564 can be relatively fixed to the supporting structure 20 by the button release pin 702.

The distal end of the release button 70 includes a resisting end 704 for mating with the rear link 564. When pressing the release button 70, the front link 562 and the rear link 564 will be driven by the resisting end 704 to move toward a status with the angle less than 180 degrees. It means that the connecting portion of the front link 562 and the rear link 564 move at the bottom side of the anastomosis device in order to break the stable mating status of the front link 562 and the rear link 564. As a result, the staple cartridge push rod 54 and staple cartridge assembly 32 will be pulled back to the proximal end in order to take out the apparatus from the operative site.

If it is desired to reuse the anastomosis device for the next cutting and anastomosis, it is achievable by replacing a new staple cartridge assembly 32 and/or an anvil assembly 34. However, it is possible in surgical process that due to the error of operator, the staple cartridge assembly 32 is triggered again before being replaced. Under this condition, the fired staple cartridge assembly 32 only contains the cutter 328 to cut the physiological tissue, but lacks of staples to anastomosis the physiological tissue, which will cause surgery accident. Thus, a safety structure will be set in the present application to facilitate avoiding such accident.

Figure 4:
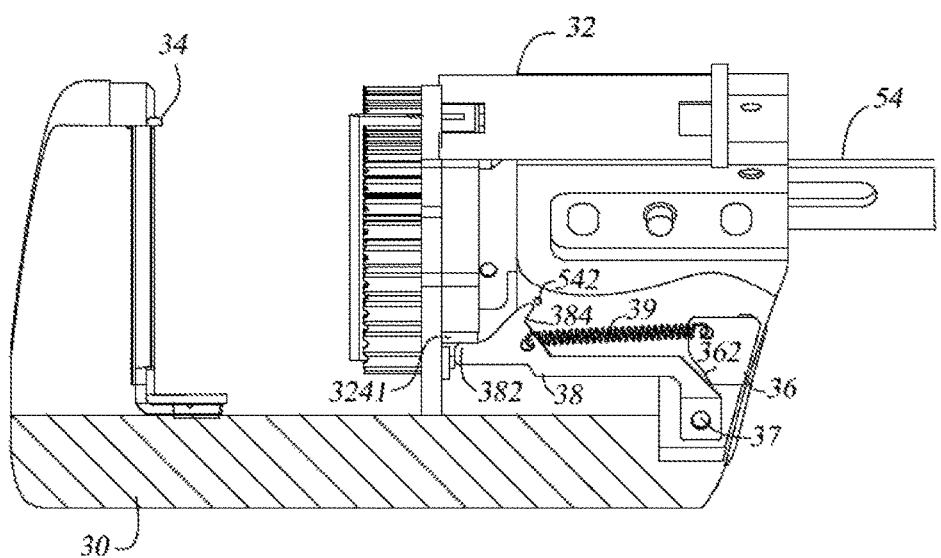
FIG. 4 is a partial cross-sectional view of the medical anastomosis device when it is located in an initial status in accordance with an illustrated embodiment of the present application.
Figure 5:
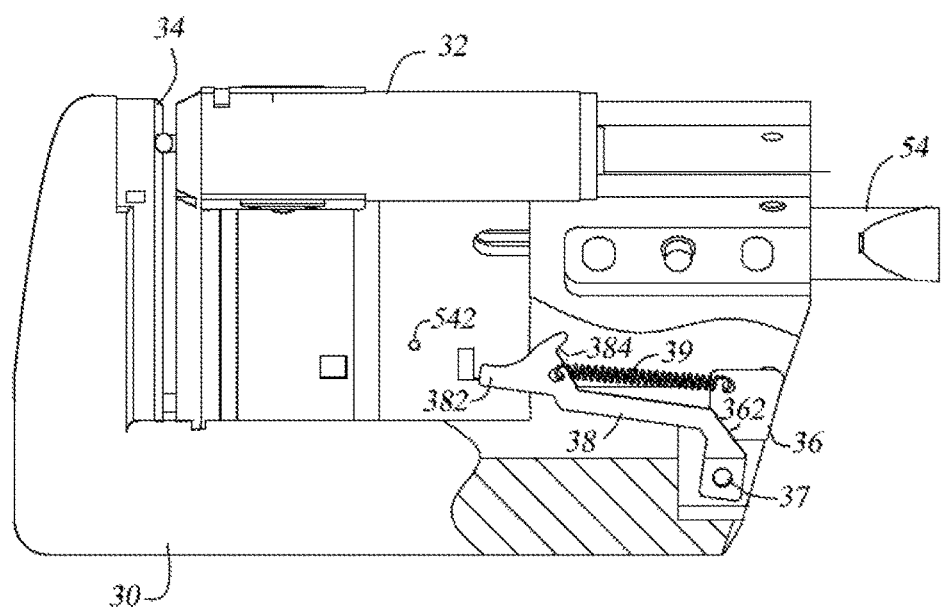
FIG. 5 is a partial cross-sectional view of the medical anastomosis device when it is located in a firing status in accordance with an illustrated embodiment of the present application.
Figure 6:
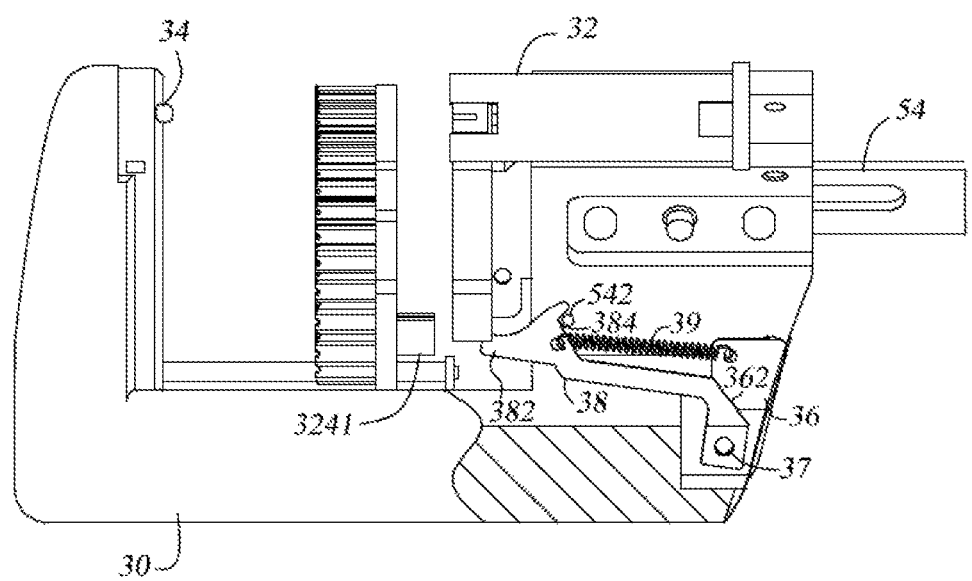
FIG. 6 is a partial cross-sectional view of the medical anastomosis device when it is in an opening status after being completely fired in accordance with an illustrated embodiment of the present application.

Referring to FIGS. 4 to 6, in an embodiment of the present application, the staple cartridge push rod 54 is provided with a banking pin 542, and a movable safety block 38 mated with the banking pin 542 is disposed in the anvil seat 30. The safety block 38 includes a slot 384. The anvil seat 30 is provided therein a safety block seat 36 for mounting the safety block 38 which is pivotally connected with the safety block seat 36. The safety block seat 36 further includes a restriction portion 362. When the anastomosis device 100 is in an initial status with the staple cartridge assembly 32 assembled to the anvil seat 30 (shown in FIG. 4), the safety block 38 does not interfere with the banking pin 542 and the restriction portion 362. Under this condition, the staple cartridge push rod 54 can be pushed to move toward the distal end by pressing the firing handle 52 so as to drive the staple cartridge assembly 32 moving to the distal end and ultimately close the anastomosis device 100 (shown in FIG. 5). The banking pin 542 moves to the farthest distal end. The safety block 38 is resisting against the restriction portion 362. The slot 384 is located in a movement route of the banking pin 542 when the banking pin 542 moves from the distal end of the medical anastomosis device 100 to the proximal end of the medical anastomosis device 100. Under this circumstance, the banking pin 542 is still not interfered with by the safety block 38. In the firing process, the position relationship of the safety block 38, the slot 384 and the restriction portion 362 remain unchanged in comparison to the status when the anastomosis device 100 is closed. When the anastomosis device 100 is of an opening status after being completely fired (shown in FIG. 6), the staple cartridge push rod 54 is drawn back into the initial position from its distal end under the effect of the release button 70. The banking pin 542 moves from its distal end to its proximal end and is ultimately locked in the slot 384. The safety block 38 will limit the banking pin 542 along a direction from the proximal end to the distal end of the anastomosis device 100. As a result, movement of the staple cartridge push rod 54 can be restricted and secondary firing of the anastomosis device 100 can be avoided. It is noted that the angle of the slot 384 should be arranged to avoid departing from the slot 384 when force is applied to the banking pin 542.

Referring to FIG. 4, when the anastomosis device 100 is in the initial status with the staple cartridge assembly 32 assembled to the anvil seat 30. The safety block 38 does not interfere with the banking pin 542. The slot 384 is separate from the banking pin 542. Movement of the staple cartridge push rod 54 is not restricted by the safety block 38. Under this condition, the staple cartridge assembly 32 can be driven by the staple cartridge push rod 54 and the pin push rod 58 to freely move to the distal end. Accordingly, the staple pusher 324 of the staple cartridge assembly 32 is provided with a first limiting portion 3241 which is located at the distal end of the banking pin 542. Specifically, when the anastomosis device 100 is in the initial status with the staple cartridge assembly 32 assembled to the anvil seat 30, the distal end of the safety block 38 is of interference with the first limiting portion 3241 of the staple pusher 324 in order to limit the rotation of the safety block 38. In an embodiment, that the distal end of the safety block 38 is provided with a second limiting portion 382. When the staple cartridge assembly 32 is in an initial status, the first limiting portion 3241 and the second limiting portion 382 can be interfered with each other. In the present embodiment, the first limiting portion 3241 includes a first part and a second part respectively located at opposite sides of the cutter slot 3242.

Referring to FIG. 5, when the anastomosis device 100 is in firing status, the pin push rod 58 moves from the proximal end to the distal end thereof under the acting force of the firing handle 52. The staple pusher 324 and the cutter 328 are pushed to move to the distal end simultaneously. The first limiting portion 3241 of the staple pusher 324 loses its interference effect to the safety block 38 so that the safety block 38 pivotally rotates until the restriction portion 362 abutting against the safety block 38 to stop further rotation of the safety block 38. In the firing process of the anastomosis device, all or part of the structure of the slot 384 move to the movement route of the banking pin 542 to ensure that the banking pin 542 can be locked in the slot 384 when the staple cartridge push rod 54 is pulled back, and the distal end of the safety block 38 is deviated from the movement route of the banking pin 542 so as to make sure that the staple cartridge push rod 54 can return.

Referring to FIG. 6, the anastomosis device 100 is under opening status after being completely fired, the staple cartridge push rod 54 will move from the distal end toward the proximal end of the anastomosis device 100 and return back to the initial position by pressing the release button 70. When the cutter assembly is driven by the staple cartridge push rod 54 to move from the distal end of the anvil seat 30 to the proximal end, the staple pusher 324 which has been fired to the distal end of the staple cartridge 322 will not generate relative displacement in the staple cartridge 322. That is when the staple cartridge assembly 32 is under a completely fired status, the first limiting portion 3241 of the staple pusher 324 will not return back to a position which will interfere with the distal end of the safety block 38. However, the banking pin 542 of the staple cartridge push rod 54 will be forced to move toward the proximal end of the safety block 38 until to be locked with the slot 384 of the safety block 38.

Figure 7:
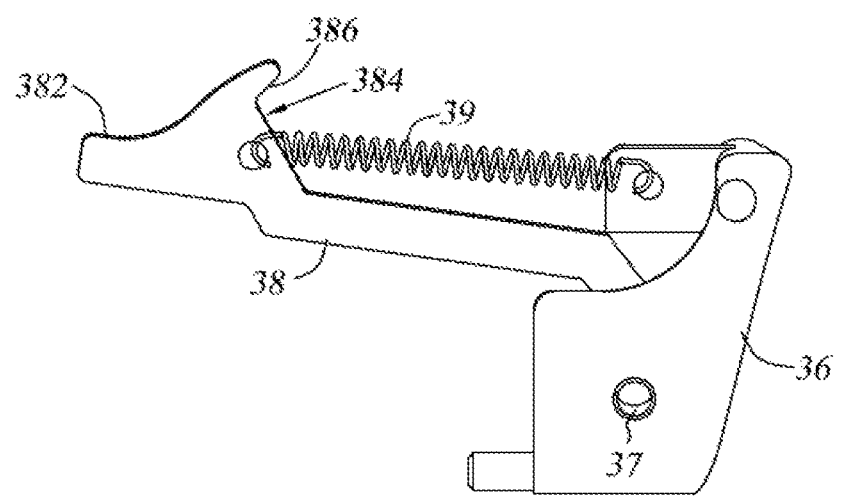
FIG. 7 is a perspective view of a safety block and a safety block seat assembled together in accordance with an illustrated embodiment of the present application.
Figure 8:
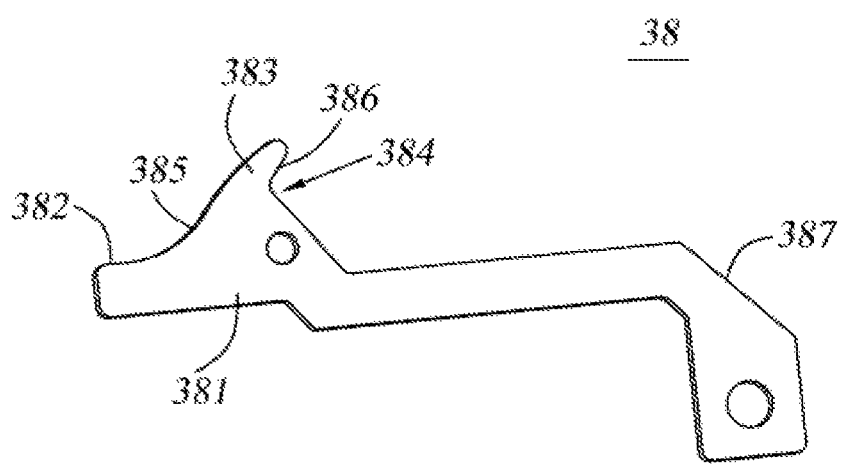
FIG. 8 is a perspective view of the safety block in accordance with an illustrated embodiment of the present application.
Figure 9:
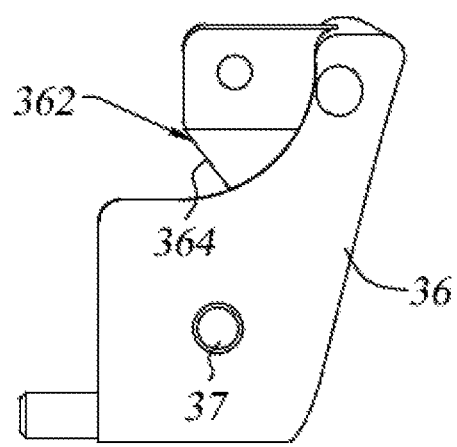
FIG. 9 is a perspective view of the safety block seat in accordance with an illustrated embodiment of the present application.

Referring to FIGS. 7 to 9, in order to facilitate the realization of above-mentioned actions, the safety block 38 includes a block body 381 and a locking portion 383 extending from the block body 381. The locking portion 383 and the block body 381 jointly define the slot 384. In an embodiment, the opening of slot 384 faces towards the proximal end of the anastomosis device 100. A side of the locking portion 383 facing the distal end of the block body 381 includes a guiding ridge 385. An angle between the guiding ridge 385 and the block body 381 is an obtuse angle. It should be noted that the "obtuse angle" mentioned herein is for explaining an expansion angle between the guiding ridge 385 and the block body 381 is larger than a vertical angle, but it should not be limited a connecting portion of the guiding ridge 385 and the block body 381 is sharp. In contrary, the connecting portion of the guiding ridge 385 and the block body 381 is of arc transition in order to better guide the banking pin 542 to be engaged in the slot 384 through the guiding ridge 385.

When anastomosis device 100 is switched among the initial status, the firing status and the opening status after being completely fired, the safety block 38 performs as a driving part. In particularly, as being driven to rotate, different mating status can be achieved to mate with the staple cartridge assembly 32 and the staple cartridge push rod 54.

The anvil seat 30 includes the safety block seat 36 for mounting the safety block 38. The safety block 38 is pivotally connected with the safety block seat 36. Specifically, the safety block 38 and the safety block seat 36 include corresponding mounting holes (not shown). A pivotal axis 37 extends through the mounting holes to connect the safety block 38 and the safety block seat 36. Meanwhile, in order to realize the pivotal rotation of the safety block 38, a torsion spring for example can be provided on the pivotal axis 37 to actuate the safety block 38. Alternatively and preferably, in the present embodiment, it is also achievable by employing a flexible member 39 connected between the safety block 38 and the safety block seat 36. The flexible member 39 consistently gives the safety block 38 a pivotal force so that the distal end of the safety block 38 can generate a trend to move toward the proximal end of the anastomosis device 100 all the time.

In an embodiment, the above-mentioned restriction portion 362 is formed on the safety block seat 36. The safety block 38 includes a first supporting surface 387, and the restriction portion 362 includes a second supporting surface 364 which alternatively resists against the first supporting surface 387. When the anastomosis device 100 is in the initial status, the first supporting surface 387 and the second supporting surface 364 form an angle. When the anastomosis device 100 is in the firing status, the first supporting surface 387 and the second supporting surface 364 are abutting against each other in order to restrict movement of the safety block 38. When the anastomosis device 100 is in the opening status after being completely fired, which means in the process when the staple cartridge assembly 32 is pulled back to the initial position by the staple cartridge push rod 54, the banking pin 542 mates with the slot 384 under the guidance of the guiding ridge 385, the safety block 38 is forced to rotate so that the first supporting surface 387 and the second supporting surface 364 are separated momently until the anastomosis device 100 is completely opened. That is when the staple cartridge assembly 32 returns back to the initial status, the first supporting surface 387 and the second supporting surface 364 abut against each other once again. Of course, in other embodiments, when the anastomosis device 100 is in the opening status after completely being fired, the first supporting surface 387 and the second supporting surface 364 are not necessarily to abut against each other. It only needs to facilitate the mating of the slot 384 and the banking pin 542. The above-mentioned embodiment illustrates only one embodiments, and should not be restricted.

Figure 10:
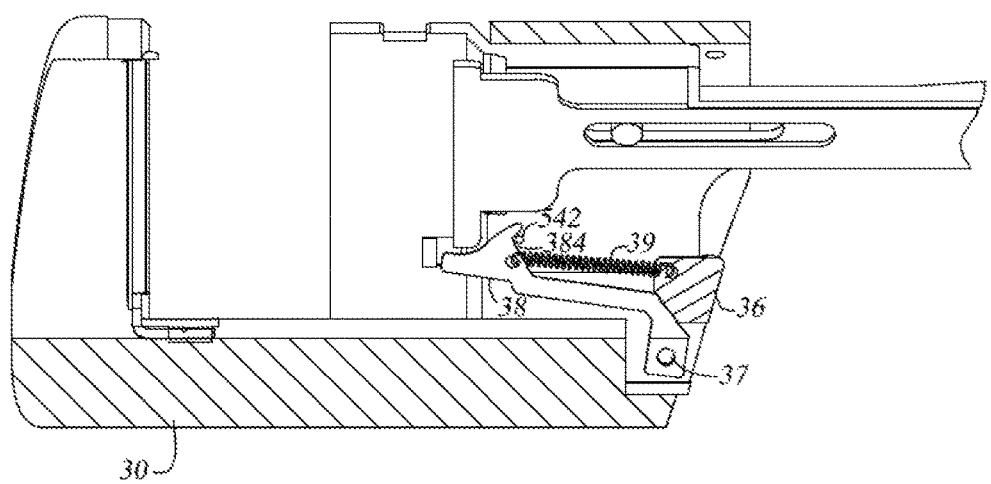
FIG. 10 is a partial cross-sectional view of the medical anastomosis device without loading the anvil assembly in accordance with an illustrated embodiment of the present application.

Referring to FIGS. 8 to 10, in the present embodiment, the slot 384 includes therein a guiding face 386 which is so arranged, when the banking pin 542 is locked in the slot 384, the banking pin 542 and the slot 384 can be separated from each other under the effect of the safety block 38 through a mounting force along the mounting direction. When the staple cartridge assembly 32 is taken off by the user after it has been fired, the slot 384 of the safety 38 is mated with the banking pin 542. During replacing new staple cartridge assembly 32, the user does not need to pay attention to the mating status of the banking pin 542 and the slot 384. The first limiting portion 3241 of the staple pusher 324 in the new staple cartridge assembly 32 will engage with the distal end of the safety block 38, which makes the slot 384 deviated from the banking pin 542. As a result, it is ensured that when the staple cartridge assembly is completely replaced, the apparatus can fire smoothly.

During the use of the medical anastomosis device 100 of the present application, the staple cartridge assembly 32 is firstly mounted to the anvil seat 30 (status shown in FIG. 4). The first limiting portion 3241 of the staple pusher 324 in the staple cartridge assembly 32 will engage with the distal end of the safety block 38 so that the safety block 38 will not in contact with the banking pin 542 of the staple cartridge push rod 54. The firing assembly 50 can apply force to the staple cartridge push rod 54 in order to close the staple cartridge assembly 32 relative to the anvil assembly 34 and to fire the staple cartridge assembly 32. When the anastomosis device 100 is closed (status shown in FIG. 5) and in the process from the staple cartridge assembly 32 to be fired and after being fired, the first limiting portion 3241 of the staple pusher 324 will gradually disengage with the safety block 38. Meanwhile, under the stretching action of the flexible member 39, the safety block 38 rotates, which causes the movement route of the banking pin 542 between the distal end of the safety block 38 and the locking portion 383. As a result, when the staple cartridge push rod 54 smoothly returns back, it is ensured that the banking pin 542 can engage with the slot 384. When once a cutting and anastomosis is completed, the staple cartridge assembly 32 is pulled back to the proximal end of the anvil seat 30 again, which means the anastomosis device 100 is of an opening status after being completely fired (status shown in FIG. 6). In the process of returning back to this status, the banking pin 542 crosses the locking portion 383 along the guiding ridge 385 to ultimately engage in the slot 384. As a result, the staple cartridge assembly 32 which has been fired can be prevented from being fired again so that the operation safety is ensured.

Figure 11:
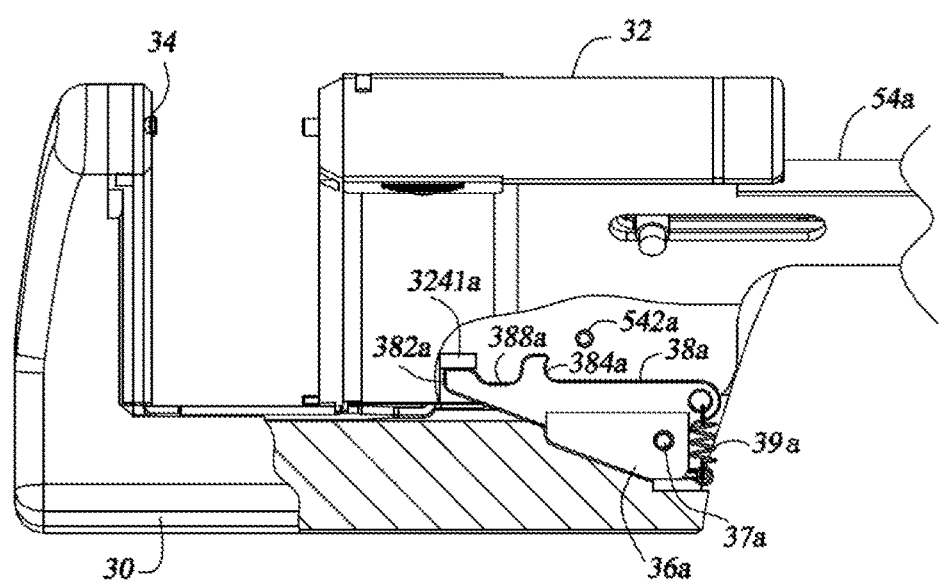
FIG. 11 is a partial cross-sectional view of the medical anastomosis device when the anvil assembly is in an initial status in accordance with an illustrated embodiment of the present application.
Figure 12:
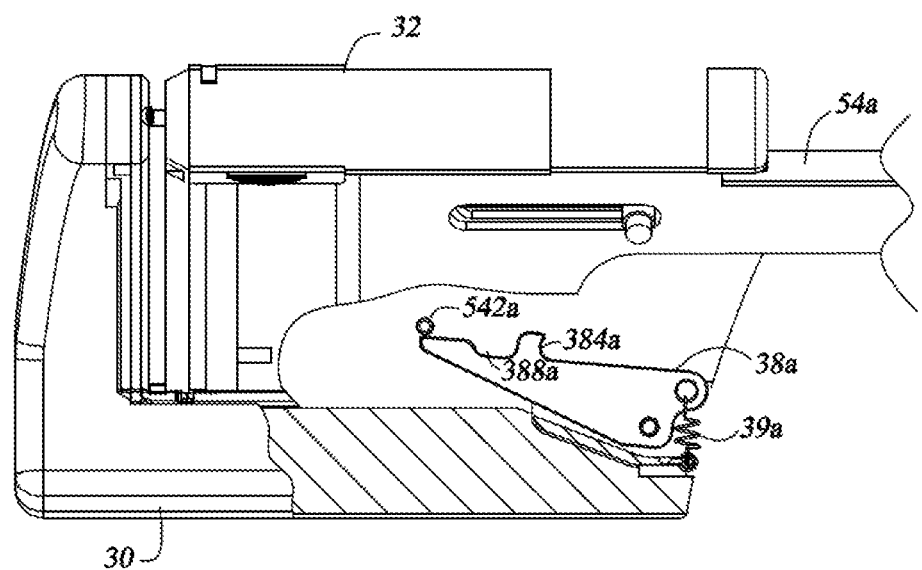
FIG. 12 is a partial cross-sectional view of the medical anastomosis device when the anvil assembly is in a firing status in accordance with an illustrated embodiment of the present application.
Figure 13:
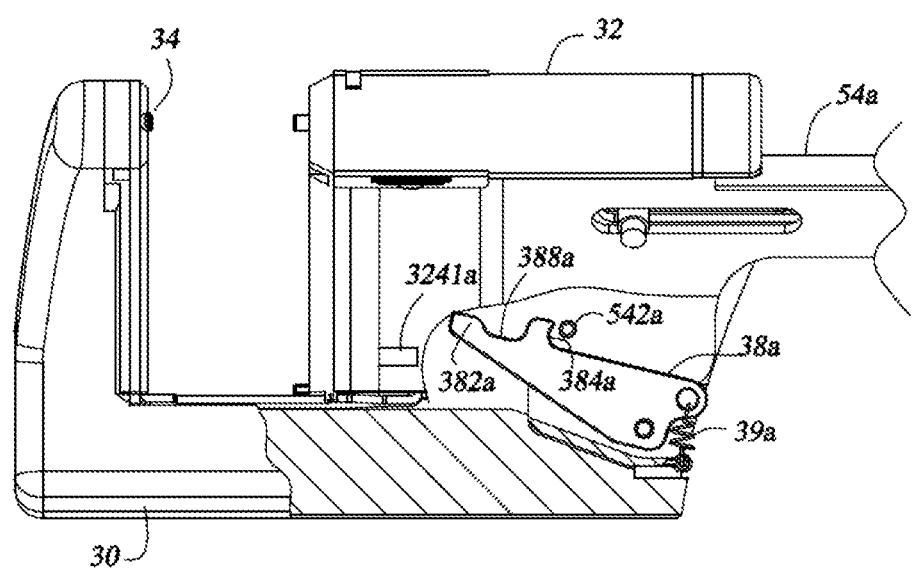
FIG. 13 is a partial cross-sectional view of the medical anastomosis device when the anvil assembly is in a completely fired status in accordance with an illustrated embodiment of the present application.

Referring to FIGS. 11 to 13, in another embodiment of the present application, the staple cartridge push rod 54a is provided with a banking pin 542a, and the anvil seat 30 is connected therein a movable safety block 38a to mate with the banking pin 542a. The safety block 38a includes a slot 384a. When the staple cartridge assembly 32 is in an initial status (shown in FIG. 11), the safety block 38a does not interfere with the banking pin 542a. When the staple cartridge assembly 32 is in a firing status (shown in FIG. 12), the banking pin 542a is engaging between the distal end of the safety block 38a and the slot 384a (the part of numeral 388a). When the staple cartridge assembly 32 is in a completely fired status (shown in FIG. 13), the banking pin 542a is engaged in the slot 384a. The banking pin 542a is restricted by the safety block 38a along the proximal end to the distal end of the anastomosis device 100, so that the movement of the staple cartridge push rod 54a can be restricted and secondary firing of the anastomosis device 100 can be avoided. It is noted that the angle of the slot 384a should be arranged to avoid departing from the slot 384a when force is applied to the banking pin 542a.

Referring to FIG. 11, when the staple cartridge assembly 32 is in the initial status, the safety block 38a does not interfere with the banking pin 542a. The slot 384a is separate from the banking pin 542a. Movement of the staple cartridge push rod 54a is not restricted by the safety block 38a. Under this condition, the staple cartridge assembly 32 can be driven by the staple cartridge push rod 54a and the pin push rod 58 to be freely fired. Accordingly, the staple pusher 324 of the staple cartridge assembly 32 is provided with a first limiting portion 3241a which is located at the distal end of the banking pin 542a. When the staple cartridge assembly 32 is in the initial status, the distal end of the safety block 38a is of interference with the first limiting portion 3241a in order to limit the rotation of the safety block 38a. In an embodiment, the distal end of the safety block 38a is provided with a second limiting portion 382a. When the staple cartridge assembly 32 is of an initial status, the first limiting portion 3241a and the second limiting portion 382a of the safety block 38a can be interfered with each other.

Referring to FIG. 12, when the staple cartridge assembly 32 is in firing status, the first limiting portion 3241a of the staple pusher 324 loses its interference effect to the safety block 38a so that the safety block 38a pivotally rotates until the banking pin 542a and the distal end of the safety block 38a interfere the slot 384a to stop further rotation of the safety block 38a. It is noted that the "firing status" includes an entire process from the staple cartridge assembly 32 being fired from the proximal end of the anvil seat 30 to the cutter 328 and the cutter rest 326 being pulled back to the proximal end of the staple cartridge assembly 32.

Referring to FIG. 13, the staple cartridge assembly 32 is under opening status after being completely fired, when the staple cartridge assembly 32 is driven by the staple cartridge push rod 54a to move from the distal end of the anvil seat 30 to the proximal end by pressing the release button 70, the staple pusher 324 will not generate relative displacement in the staple cartridge 322. That is when the staple cartridge assembly 32 is under a completely fired status, the first limiting portion 3241a of the staple pusher 324 will not return back to a position which will interfere the distal end of the safety block 38a. However, the banking pin 542a of the staple cartridge push rod 54a will be forced to move toward the proximal end of the safety block 38a until to be locked with the slot 384a of the safety block 38a. In such process, the safety block 38a continues to rotate in order to ensure sufficient and reliable mating of the slot 384a and the banking pin 542a.

Figure 14:
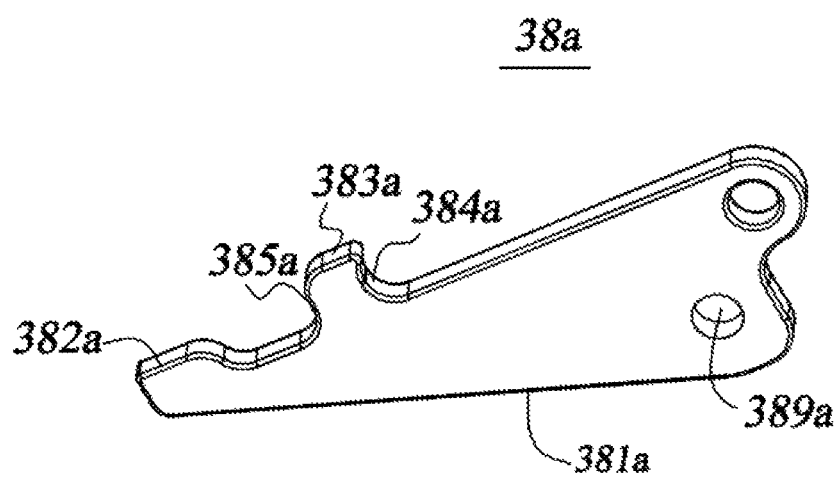
FIG. 14 is a perspective view of a safety block in accordance with a second illustrated embodiment of the present application.

Referring to FIG. 14, in order to ensure the smooth enforcement of above-mentioned actions, the safety block 38a includes a block body 381a and a locking portion 383a extending from the block body 381a. The locking portion 383a and the block body 381a jointly define the slot 384a. In an embodiment, the opening of slot 384a faces towards the proximal end of the medical anastomosis device 100. A side of the locking portion 383a facing the distal end of the block body 381a includes a guiding ridge 385a. An angle between the guiding ridge 385a and the block body 381a is an obtuse angle. It should be noted that the "obtuse angle" mentioned herein is for explaining an expansion angle between the guiding ridge 385a and the block body 381a is larger than a vertical angle, but it should not be limited a connecting portion of the guiding ridge 385a and the block body 381a is sharp. In contrary, the connecting portion of the guiding ridge 385a and the block body 381a is of arc transition in order to better guide the banking pin 542a to be engaged in the slot 384a through the guiding ridge 385a.

When the staple cartridge assembly 32 is switched among the initial status, the firing status and the opening status after being completely fired, the safety block 38a performs as a driving part. In particularly, as being driven to rotate, different mating status can be achieved to mate with the staple cartridge assembly 32 and the staple cartridge push rod 54a.

The safety block 38a is pivotally connected to the anvil seat 30. Specifically, the safety block 38a includes a first mounting hole 389a, and the anvil seat 30 includes therein a pivotal axis 37a for mating with the first mounting hole 389a. The safety block 38a is pivotally mounted to the pivotal axis 37a through the first mounting hole 389a. In order to realize the pivotal rotation of the safety block 38a, a torsion spring for example can be provided on the pivotal axis 37a to actuate the safety block 38a. Alternatively, in the present embodiment, it is also achievable by employing a flexible member 39a connected between the safety block 38a and the anvil seat 30. The flexible member 39a consistently provides the safety block 38a a pivotal force to drive the distal end of the safety block 38a to move towards the proximal end of the anastomosis device 100. The flexible member 39a is connected to the proximal end of the safety block 38a. The first mounting hole 389a is located between the proximal end and the distal end of the safety block 38a. When the staple cartridge assembly 32 is in the initial status, the flexible member 39a is under an extended status. The "flexible member 39a" mentioned herein is an elastic stretching element which can be stretched. In comparison with the torsion spring, the actuating of this elastic stretching element is much reliable.

Figure 15:
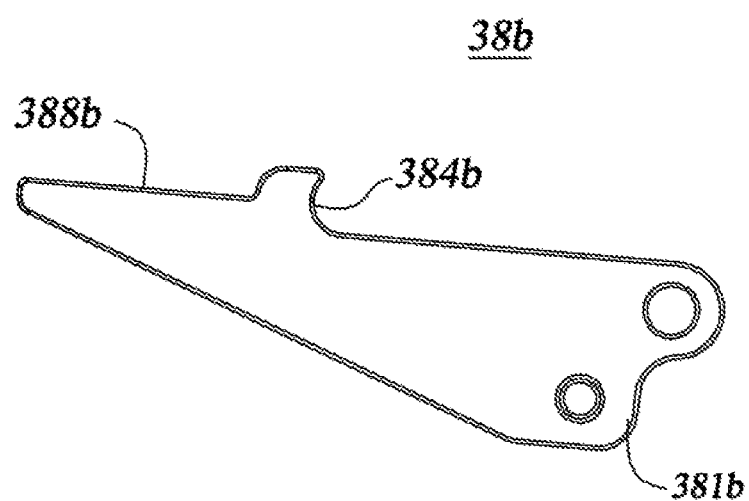
FIG. 15 is a perspective view of a safety block in accordance with a third illustrated embodiment of the present application.

Referring to FIG. 15, another embodiment of the safety block 38b is disclosed. In the present embodiment, the safety block 38b includes a block body 381b which is provided with a slot 384b similar to the slot 384a shown in the previous embodiment. The difference therebetween is the distal end of the block body 381b does not include a protruded supporting portion. The slot 384b and the distal end of the block body 381b are flat and aligned with each other, which can also meet actual requirements.

Figure 16:
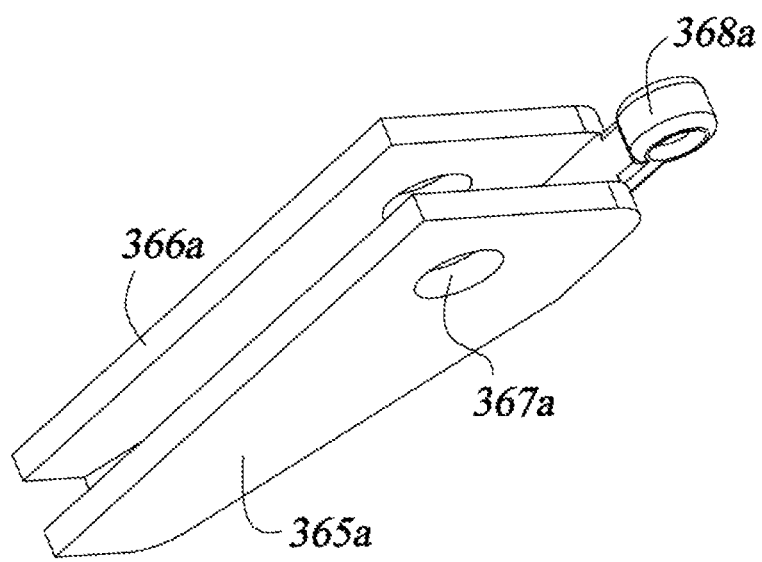
FIG. 16 is a perspective view of a safety block seat in accordance with another illustrated embodiment of the present application.

Referring to FIG. 16, in an embodiment, the anvil seat 30 includes therein a detachable safety block seat 36a. The safety block seat 36a is relatively fixed to the anvil seat 30 and is pivotally connected to the anvil seat 30. The safety block seat 36a includes a mounting portion 368a. Two ends of the flexible member 39a are respectively connected to the proximal end of the safety block 38a and the mounting portion 368a. Because the safety block seat 36a is detachable, it is much easier to mount the safety block 38a and corresponding parts can be replaceable. The safety block seat 36a includes a first mounting plate 365a and a second mounting plate 366a opposite to the first mounting plate 365a. At least part of the safety block 38a is mounted between the first mounting plate 365a and the second mounting plate 366a. The first mounting plate 365a and the second mounting plate 366a respectively include a second mounting hole 367a for mating with the pivotal axis 37a. The pivotal axis 37a extends through the first mounting hole 389a and the second mounting hole 367a respectively to fix the relative position of the first mounting hole 389a and the second mounting hole 367a along the axis direction.

During the use of the medical anastomosis device 100 of the present application, the staple cartridge assembly 32 is firstly mounted to an initial status (status shown in FIG. 11). The first limiting portion 3241a of the staple cartridge assembly 32 will engage with the distal end of the safety block 38a so that the safety block 38a will not in contact with the banking pin 542a of the staple cartridge push rod 54a. The firing assembly 50 can apply force to the staple cartridge assembly 32 and fire the staple cartridge assembly 32. When the anastomosis device 100 is closed (status shown in FIG. 12) and in the process from the staple cartridge assembly 32 to be fired and after being completely fired, under condition when the staple cartridge assembly 32 is fired, the first limiting portion 3241a in the staple cartridge assembly 32 disengages with the safety block 38a. Meanwhile, under the stretching action of the flexible member 39a, the safety block 38a rotates, which makes the banking pin 542a of the staple cartridge push rod 54a engages between the distal end of the safety block 38a and the slot 384a. When once a cutting and anastomosis is completed, the staple cartridge assembly 32 is pulled back to the proximal end of the anvil seat 30 again, which means the anastomosis device 100 is of an opening status after being completely fired (status shown in FIG. 13). In the process of returning back to this status, the safety block 38a continues to rotate driven by the flexible member 39a so that the slot 384a gradually engages with the banking pin 542a. As a result, the staple cartridge push rod 54a can be prevented from being fired again so that the operation safety is ensured.

For those skilled in the art, apparently, the present disclosure should not be limited to the detailed of these exemplary embodiments, and embodiments can be realized by other concrete forms. Therefore, no matter from which point of view, the embodiments should be regarded as exemplification rather than restriction.

In addition, it is to be understood, however, that even though exemplary embodiments have been set out in the foregoing description, it does not mean that each embodiment has only one independent technical solution. The narration of the specification is only for clear description. Those of ordinary skill in the art should consider the specification as a whole. Technical solutions of all the embodiments can be appropriately combined to form other embodiments which are understandable by those skilled in the art.

What is claimed is:

1. A medical anastomosis device comprising:
   a firing assembly comprising a staple cartridge push rod and a banking pin;
   an anvil seat comprising a safety block to mate with the banking pin, the safety block defining a slot;
   an anvil assembly; and
   a staple cartridge assembly; wherein, in operation,
   the firing assembly is used for driving the staple cartridge assembly to move from a proximal end of the anvil seat to a distal end of the anvil seat;
   when the medical anastomosis device is in an initial status, the safety block does not interfere with the banking pin;
   when the medical anastomosis device is in a firing status, movement of the safety block is restricted, and the slot is located in a movement route of the banking pin when the banking pin moves from a distal end of the medical anastomosis device to a proximal end of the medical anastomosis device; and
   when the medical anastomosis device returns to the initial status after being completely fired, the banking pin is locked in the slot and restricted by the safety block along a direction from the proximal end of the medical anastomosis device to the distal end of the medical anastomosis device.

2. The medical anastomosis device as claimed in claim 1, wherein the anvil seat comprises therein a restriction portion to mate with the banking pin; wherein, in operation,
   when the medical anastomosis device is in the initial status, the safety block does not interfere with the restriction portion; and
   when the medical anastomosis device is in the firing status, the safety block abuts against the restriction portion.

3. The medical anastomosis device as claimed in claim 2, wherein the safety block is configured to consistently receive a pivotal force which drives a distal end of the safety block to move toward the proximal end of the medical anastomosis device.

4. The medical anastomosis device as claimed in claim 3, wherein the anvil seat comprises therein a safety block seat to mount the safety block, the safety block is pivotally connected to the safety block seat, and the restriction portion is formed on the safety block seat.

5. The medical anastomosis device as claimed in claim 4, wherein a flexible member is connected between the safety block and the safety block seat.

6. The medical anastomosis device as claimed in claim 2, wherein the slot comprises therein a guiding face which is so arranged, when the banking pin is locked in the slot, that the banking pin and the slot can be disengaged with each other by the safety block through a force along a mounting direction of the staple cartridge assembly.

7. The medical anastomosis device as claimed in claim 1, wherein when the staple cartridge assembly is in a firing status, the banking pin is resisted between a distal end of the safety and the slot.

8. The medical anastomosis device as claimed in claim 7, wherein the safety block is pivotally connected to the anvil seat, and a flexible member is connected between the safety block and the anvil seat.

9. The medical anastomosis device as claimed in claim 8, wherein the flexible member consistently provides the safety block a pivotal force to drive the distal end of the safety block to move towards the proximal end of the anastomosis device.

10. The medical anastomosis device as claimed in claim 9, wherein the anvil seat comprises therein a detachable safety block seat, the safety block seat being relatively fixed to the anvil seat, the safety block seat being pivotally connected to the anvil seat, the safety block seat being provided with a mounting portion, two ends of the flexible member being respectively connected to the safety block and the mounting portion.

11. The medical anastomosis device as claimed in claim 10, wherein the safety block seat comprises a first mounting plate and a second mounting plate opposite to the first mounting plate, at least part of the safety block being mounted between the first mounting plate and the second mounting plate.

12. The medical anastomosis device as claimed in claim 11, wherein the safety block defines a first mounting hole, the first mounting plate and the second mounting plate respectively defining a second mounting hole, the medical anastomosis device further comprising a pivotal axis which extends through the first mounting hole and the second mounting hole so as to fix the relative position of the first mounting hole and the second mounting hole along an axis direction.

13. The medical anastomosis device as claimed in claim 1, wherein the staple cartridge assembly comprises a staple pusher which is provided with a first limiting portion located at a distal end of the banking pin; a distal end of the safety block comprises a second limiting portion; when the medical anastomosis device is in the initial status, the second limiting portion of the safety block is interfered with the first limiting portion of the staple pusher.

14. The medical anastomosis device as claimed in claim 13, wherein the staple pusher defines a cutter slot, and the first limiting portion comprises a first part and a second part respectively located at opposite sides of the cutter slot.

15. The medical anastomosis device as claimed in claim 1, wherein the safety block comprises a block body and a locking portion extending from the block body, the locking portion and the block body jointly defining the slot, an opening of slot facing towards the proximal end of the medical anastomosis device.

16. The medical anastomosis device as claimed in claim 15, wherein a side of the locking portion facing a distal end of the block body comprises a guiding ridge, an angle between the guiding ridge and the block body being an obtuse angle.

17. The medical anastomosis device as claimed in claim 16, wherein a connecting portion of the guiding ridge and the block body circular is of arc transition.

* * * * *